United States Patent [19]

Speidel

[11] 4,240,297

[45] Dec. 23, 1980

[54] PRESSURE GAUGE FOR SPHYGMOMANOMETERS

[76] Inventor: Blasius Speidel, Hochmeisterstrasse 33, 7455 Jungingen, Fed. Rep. of Germany

[21] Appl. No.: 23,410

[22] Filed: Mar. 23, 1979

[30] Foreign Application Priority Data

Mar. 23, 1978 [DE] Fed. Rep. of Germany ....... 2812755

[51] Int. Cl.³ .............................................. G01L 7/08
[52] U.S. Cl. ........................................ 73/711; 73/715
[58] Field of Search ................ 73/715, 716, 711, 729, 73/386, 387, 432 A; 116/289; 73/748

[56] References Cited

U.S. PATENT DOCUMENTS

| | | | |
|---|---|---|---|
| 1,411,917 | 4/1922 | Harris | 73/715 |
| 1,666,787 | 4/1928 | Michelin | 73/715 |
| 2,194,624 | 3/1940 | Titterington, Jr. | 73/729 |
| 4,036,061 | 7/1977 | Speidel | 73/729 |

*Primary Examiner*—Donald O. Woodiel
*Attorney, Agent, or Firm*—Joseph A. Geiger

[57] ABSTRACT

A pressure gauge for sphygmomanometers, having a pressure capsule with a diaphragm wall, a pointer on a rotatable spring-biased pointer shaft, and a drive mechanism connecting the diaphragm wall to the pointer shaft by picking up and magnifying the displacements of the diaphragm wall, the drive mechanism including a sensing member on a rotatable sensing shaft, in contact with the diaphragm wall, and a magnifying gear drive consisting of a drive arm on the sensing shaft with gear teeth forming a gear segment of large radius, in driving engagement with a pinion on the pointer shaft. The drive arm may be bendable to adjust the gear drive ratio.

12 Claims, 6 Drawing Figures

PRESSURE GAUGE FOR SPHYGMOMANOMETERS

BACKGROUND OF THE INVENTION

1. Field of the Invention

The present invention relates to pressure gauges, and, more particularly, to pressure gauges for blood pressure measuring devices, or so-called sphygmomanometers, which are designed to visually indicate the air pressure in a blood pressure measuring cuff which is attached to a limb of the person whose blood pressure is to be determined.

2. Description of the Prior Art

The measurement of a person's blood pressure, as proposed by Riva-Rocci and Korotkoff, involves the attachment of an inflatable measuring cuff to an extremity of the person under examination and the application of a pressure to that cuff, from a suitable pressure source, to a pressure level which is higher than the anticipated systolic blood pressure value. Using an adjustable deflation valve, the air pressure in the measuring cuff is then gradually reduced, while the blood circulation under the cuff is monitored through auscultation. Such auscultation reveals that, at a certain pressure in the measuring cuff, the blood circulation starts to produce characteristic rushing sounds, the so-called Korotkoff noises. This pressure level represents the systolic blood pressure. As the pressure in the measuring cuff is further lowered, it reaches a level at which these blood circulation noises disappear again. This second pressure level represents the diastolic blood pressure. This method of blood pressure examination has received widespread acceptance, because of its absence of risk to the person examined, its extreme simplicity, and its low cost.

The determination of the systolic and diastolic blood pressure levels is commonly performed visually, using a simple air pressure gauge which is connected to the measuring cuff or to the pressure hose which leads to the cuff. The prior art in this field discloses various pressure gauges for this purpose, a change in air pressure being typically converted into an angular movement of a pointer over a circular dial. Typically, the pressure gauge utilizes a flexible pressure capsule whose interior space communicates with the measuring cuff. The pressure capsule has one wall which is flexible so as to bulge outwardly, as the pressure inside the capsule increases. A suitable mechanism is used to pick up and magnify these displacements of the capsule wall, transmitting them to a spring-biased rotatable shaft which carries a pointer. This pickup and magnification mechanism includes a sensing member on a rotatably supported sensing shaft, the sensing member being a wire part, curved like a skid and bearing against the flexible wall of the pressure capsule under a spring bias. The sensing member thus transmits the expansion and contraction displacements of the pressure capsule to the sensing shaft in the form of angular displacements of the latter. A long transmission pin, extending radially from the sensing shaft and in a direction away from the pressure capsule, then transmits these displacements in magnified values to a swivel arm which is arranged in its path and supported on a pivot shaft. The latter is oriented perpendicularly to both the sensing shaft and the flexible pressure capsule wall. The far extremity of the swivel arm carries a gear segment in meshing engagement with a pinion which is mounted on the rotatably supported pointer shaft. The latter, in addition to carrying the pointer itself, also carries a spiral spring which provides the spring bias between the sensing member and the flexible wall of the pressure capsule, thereby also eliminating any transmission play.

Most sphygmomanometer pressure gauges use a circular pressure capsule whose flexible wall is a diaphragm-type wall, i.e. a large wall portion which is surrounded by circular undulations in the capsule wall. The expansion and contraction displacements of this diaphragm wall are substantially proportional to the pressure changes inside the pressure capsule. The pickup and magnification mechanism converts these displacements into much larger angular displacements of the gauge pointer. However, the two lever-type force transmissions in the magnification mechanism produce certain distortions in the transmission ratio, due to changes in the effective lengths of the lever arms, so that the displacement values shown by the pointer are no longer exactly linear in relation to the actual pressure values. Fixed pressure increments in a higher pressure range thus produce smaller pointer increments, meaning that the markings on the gauge dial have to be more closely spaced for higher pressure values. Generally, it is not a great disadvantage to have such non-linear dial markings on the pressure gauge, provided the pressure range distribution on the gauge dial remains unchanged, i.e. when the zero-position on the dial is a fixed one. To the extent that there exist small variations in this zero-position, as a result of assembly and manufacturing tolerances, these variations are negligible, in comparison to other variables which affect the accuracy of this kind of blood pressure measuring procedure.

The blood pressure values obtained in accordance with the above-described auscultatory measuring approach, as suggested by Riva-Rocci and Korotkoff, when compared to actual blood pressure values obtained through a "bloody measurement" taken inside an artery of the patient, are subject to considerable deviations from these actual pressure values, depending upon the structure of the limb on which the measurements are taken. Commonly, the auscultatory blood pressure measurements are taken on the left upper arm of a person. If that person is of a slight build, with a minimum of soft body tissue on the upper arm, for example, or if that person is of a rather heavy build, with considerable muscle and/or fatty tissue at the point of measurement, the measurements obtained by the auscultatory method may deviate from the actual blood pressure values by as much as 25 mm Hg in either direction, respectively. It has been found that the correction factors which have to be applied to the systolic and diastolic pressure values, as a result of different structures of the patient's limb, are approximately proportional to the circumference of that limb, so that a compensatory correction to obtain the actual values requires only a simple angular shift of the zero-position on the pressure gauge dial. Such a zero-position shift, however, makes it a prerequisite that the gauge dial has identical linear increments over its entire measurement range. By the same token, it follows that a zero-position shift is not possible with the above-described prior art pressure gauge.

SUMMARY OF THE INVENTION

It is a primary objective of the present invention to suggest an improved pressure gauge for blood pressure measuring devices, or sphygmomanometers, which does not have the aforementioned prior art shortcoming of a non-linear indicating dial, but has regularly divided dial markings, so that the zero-position of the latter can be adjusted by angularly shifting the dial in relation to the moving pointer.

The present invention proposes to attain this objective by suggesting an improved pressure gauge which features a pickup and magnification mechanism, or pointer drive, between the pressure capsule and the pointer shaft which, instead of using the conventional pivotable drive levers, uses a gear drive for the transmission and magnification of the pressure-induced displacements of the pressure capsule wall. While the present invention suggests the use of the earlier-described pressure capsule and cooperating sensing member on a rotatably supported sensing shaft, the novel pointer drive mechanism transmits the angular displacements of the sensing shaft without distortion to the pointer shaft, thereby maintaining the linearity of the relationship between the movements of the flexible pressure capsule wall and the pointer. Accordingly, the markings on the circular dial of the pressure gauge will have regular increments, so that it becomes possible to arrange the dial on a ring which is angularly adjustable in relation to the pointer shaft, thereby resetting the zero-position of the dial for a convenient correction of its readings, in order to compensate for the earlier-mentioned measurement distortions which result from differences in the limb structure of the person being examined.

In a preferred embodiment of the invention, the pickup portion of the pointer drive features, as a sensing member, a pin which extends radially from the sensing shaft and which carries a rounded sensing head in a spring-biased engagement with the flexible wall of the pressure capsule. The choice of an enlarged rounded sensing head has the advantage of accommodating a sensing shaft of sufficient diameter to be stiff while determining an effective length of the lever arm between the contact point on the sensing head and the axis of the sensing shaft which produces a nearly linear drive transmission over the entire range of capsule wall displacements. Ideally, the contour of the sensing head on the sensing member would be an envolute-type curve, in which case the conversion of the linear displacements of the pressure capsule wall into angular displacements of the sensing shaft would be exactly linear. The pin which carries the enlarged sensing head is preferably a threaded part, extending through a transverse threaded bore in the sensing shaft, thereby facilitating the assembly of the sensing member, while making it adjustable at minimal cost.

The magnification portion of the pointer drive as suggested by the present invention features a drive arm which is directly attached to the sensing shaft so as to move with the latter, the drive arm being in the form of a gear segment of large radius which engages a small pinion on the pointer shaft. The drive arm will take different forms, depending on whether the axis of the pointer shaft is parallel to, or arranged at right angles to the sensing shaft and to the plane of the flexible wall of the pressure capsule. In most cases, it is preferable to have a pointer shaft which is oriented perpendicularly to the pressure capsule, so that the plane of the dial is parallel to the latter, for a compact structure of the pressure gauge. In this case, the gear teeth of the drive arm and the pinion on the pointer shaft have to form an angle drive. While this requirement would normally call for bevel gears, the large difference in diameter of the two gears makes it possible to simplify the gear drive by using a cylindrical pinion and a gear segment of the cup-gear type, meaning that the gear teeth on the drive arm are oriented axially with respect to the sensing shaft, as if arranged on a segment of the extremity of a tubular body.

For the type of pressure gauge which features a pointer shaft which is parallel to the sensing shaft, the engagement between the gear sector and the pinion on the pointer shaft is a standard spur gear engagement, so that the drive arm can have the form of a flat stamping which is mounted on the sensing shaft, extending radially from the latter and having a yoke-like extremity which carries the gear teeth in engagement with the pinion on the pointer shaft.

The earlier-described drive arm which engages the pinion like a cup gear further offers certain interesting posibilities with respect to an adjustment of the drive ratio of the gears, on the one hand, and with respect to the deliberate introduction of a certain non-linearity of drive transmission, on the other hand. The latter may serve to cómpensate for any non-linearity in the pickup portion of the drive mechanism. In a preferred embodiment of the invention, it is therefore suggested that the drive arm of the mechanism be provided with an axially offset configuration, having not only a relatively long radial extension from its attachment to the sensing shaft, but also a relatively long axial extension, so that the gear teeth themselves are arranged in a radial plane which is located at a considerable axial distance from the radial portion of the drive arm. The axial length portion of the drive arm gives the latter a degree of formability, thereby making the gear drive adjustable in the following ways:

By bending the axial length portion of the drive arm radially outwardly or inwardly, the effective pitch radius of the gear segment can be increased or decreased, respectively, thereby changing the drive ratio of the two gears, for a greater or lesser magnification of the displacement values which are received from the pressure capsule. However, the drive arm must be bent parallel to itself, in order to retain the alignment of the gear teeth with a radial plane which is tangent to the pitch circle of the pinion.

By twisting the axial length portion of the drive arm and/or by bending its teeth-carrying yoke portion out of concentricity with the axis of the sensing shaft, the drive ratio between the two gears can be made non-linear, for an increase or decrease of the pressure value magnification over the entire measurement range or any portion thereof. In this manner, it is possible to compensate for any distortions which may have been introduced by the pickup portion of the drive mechanism, or for any non-linearity in the displacement response of the pressure capsule wall, so that the markings on the pointer dial will have a uniform spacing. Of course, the aforementioned adjustment features also make it possible to deliberately introduce a certain non-linearity into the response characteristics of the pressure gauge, should such a non-linear response be desirable for any reason.

In order to eliminate any play from the drive mechanism, the present invention further suggests the arrangement of the sensing shaft on axially adjustable tapered pin journals and the use of a conventional spiral spring on the pointer shaft. The latter applies a play-eliminating bias to the drive mechanism, in the sense of preloading the sensing member against the flexible wall of the pressure capsule. This arrangement also makes allowance for the necessary clearance between the teeth of the pinion and the gear teeth of the drive arm. The latter can thus be a sheet metal stamping which does not require precision-machined tooth flanks.

BRIEF DESCRIPTION OF THE DRAWINGS

Further special features and advantages of the invention will become apparent from the description following below, when taken together with the accompanying drawings which illustrate, by way of example, two embodiments of the invention which are represented in the various figures as follows.

DESCRIPTION OF THE PREFERRED EMBODIMENTS

FIGS. 1-4 illustrate a first embodiment of the present invention, represented by a blood pressure gauge whose main constituent units are a pressure capsule 10, a pointer 11, and a drive mechanism 12, the latter connecting the pressure capsule 10 to the pointer 11, through pickup and magnification of the pressure-responsive displacements of the pressure capsule 10. A plate frame 13, of which only portions are shown, supports these constituent units of the pressure gauge.

The pressure capsule 10 is of generally known construction, being mounted on a base plate 14. Opposite the base plate 14, the pressure capsule forms a flexible diaphragm wall 15 whose periphery is hermetically soldered to the base plate 14. A connector 16 in the base plate 14 (FIG. 3) leads from the pressure source (not shown) to the enclosed pressure space between the diaphragm wall 15 and the base plate 14. Structurally, the pressure gauge may be combined with the deflation valve, or with a hand-held squeeze bulb for the inflation of the blood pressure measuring cuff. Alternatively, the pressure gauge, deflation valve, and squeeze bulb may be combined in a single hand-held unit.

Figure 1:
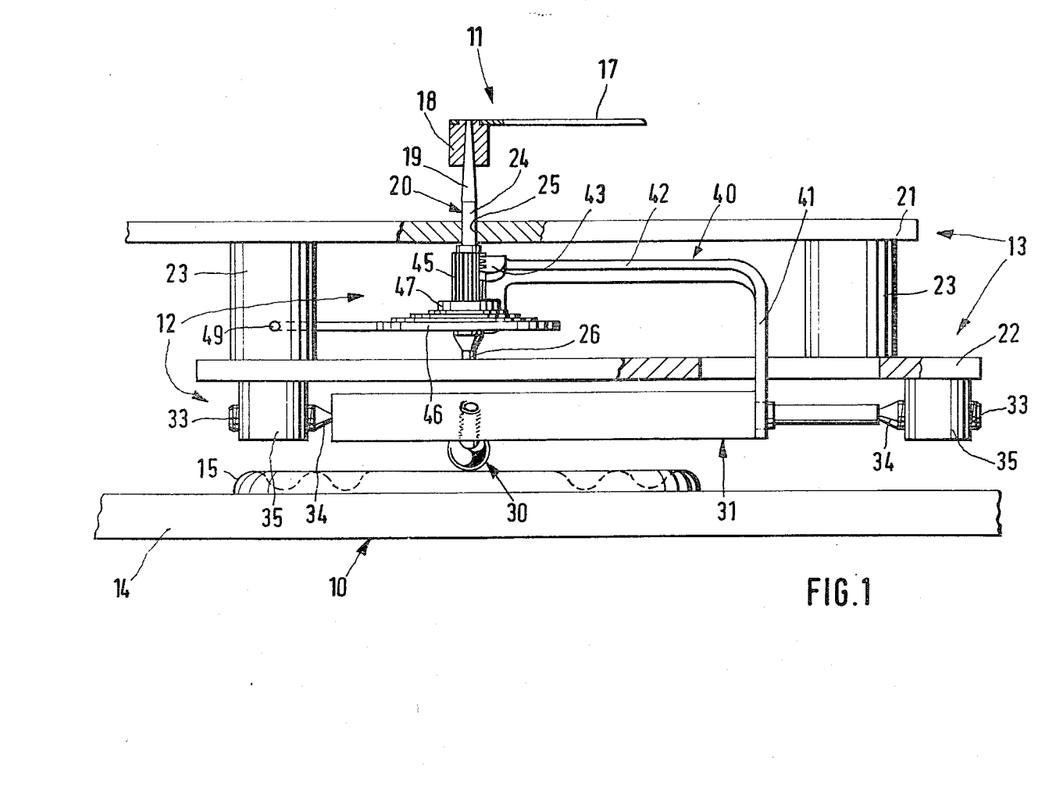
FIG. 1 shows, in elevation and partial cross section, the major components of a pressure gauge representing a first embodiment of the present invention.

The pointer 11 consists of a pointer finger 14 which extends radially from a pointer hub 18 to which it is permanently attached by an upset on the outer edge of the hub 18. A frictional taper seat between a tapered bore of the pointer hub 18 and a matchingly tapered end portion 19 of the pointer shaft 20 allows for the proper angular positioning of the pointer 11 at assembly.

Figure 3:
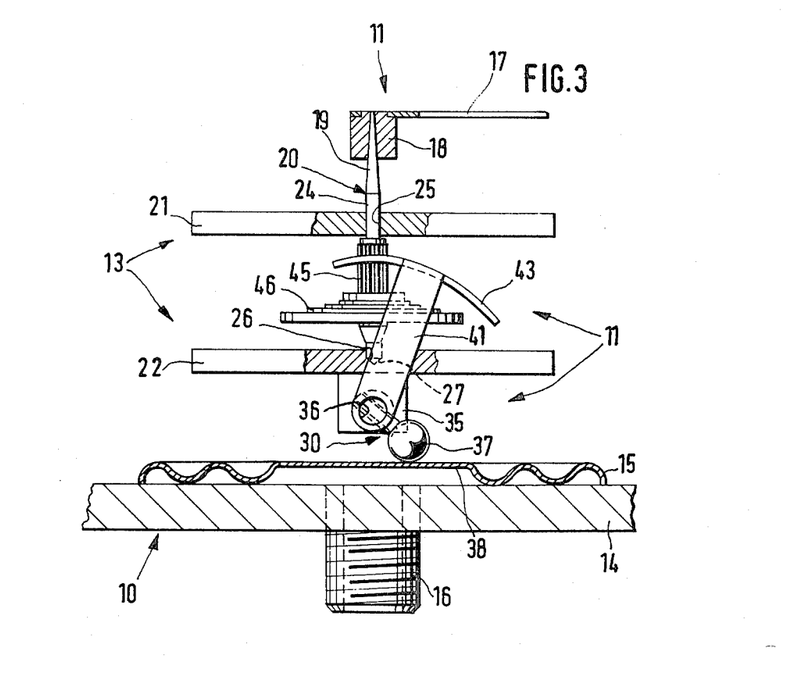
FIG. 3 shows the pressure gauge of FIG. 1 in a partially cross-sectioned side view.

The pointer shaft 20 is rotatably supported in the plate frame 13. This frame consists of an upper support plate 21 and a lower support plate 22, held together by means of several spacer posts 23. In FIG. 3, these spacer posts have been omitted, for the sake of improved clarity of the drawing. A cylindrical bearing bore 25 in the upper support plate 21 engages a matching cylindrical portion 24 of the pointer shaft 20, while a tapered blind bore 27 in the lower support plate 22 serves as a journal support for a matchingly tapered lower extremity 26 of the pointer shaft 20. Although not shown in the drawing, the plate frame 13 is rigidly connected with the base plate 14 of the pressure capsule 10.

The drive mechanism 12 of the proposed pressure gauge serves to pickup and magnify the displacements of the diaphragm wall 15 of pressure capsule 10, while transferring them to the pointer shaft 20. This drive mechanism 12 has in its pickup part a sensing member 30 which is carried by a sensing shaft 31, on a rotational axis which is parallel to the general plane of the diaphragm wall 15. The journal support for the sensing shaft 21 is provided by two axially oriented threaded bearing pins 33 and 34 with tapers 34 which engage matching center bores 32 (FIG. 2) of the sensing shaft 31. The threaded bearing pins 33 and 34 are adjustably seated in axially aligned threaded bores of two bearing blocks 35 which extend downwardly from the lower support plate 22. At assembly, the two threaded bearing pins 33 and 34 are adjusted for the correct axial position and for minimal rotational clearance of the sensing shaft 31, whereupon their threads are secured against rotation by means of a suitable glue or an adhesive lacquer.

The sensing member 30 is essentially a threaded pin which extends radially from the sensing shaft 31, being engaged in a matching threaded bore 36 of the latter. Following assembly and adjustment, the threaded pin of the sensing member 30 is secured by means of an upset or the application of glue to the threads. The distal extremity of the sensing member 30 is enlarged into a spherical sensing head 37. The latter may be an integral part of the threaded pin portion, or it may be screwed onto the extremity of the latter, having an appropriate tapped blind hole. As can be seen in FIG. 3, the sensing member 30 reaches obliquely downwardly from the center of the sensing shaft 31 so that its head 37 is in contact with the flat surface portion 38 of the diaphragm wall 15. This wall executes movements towards and away from the base plate 14, in response to pressure changes taking place inside the pressure capsule 10, which movements are then transmitted to the sensing member 30, via the curved surface of its sensing head 37. The contact point on the diaphragm wall 15 is in the vicinity of the center of the latter, so that the maximum displacement of the wall is picked up.

Figure 2:
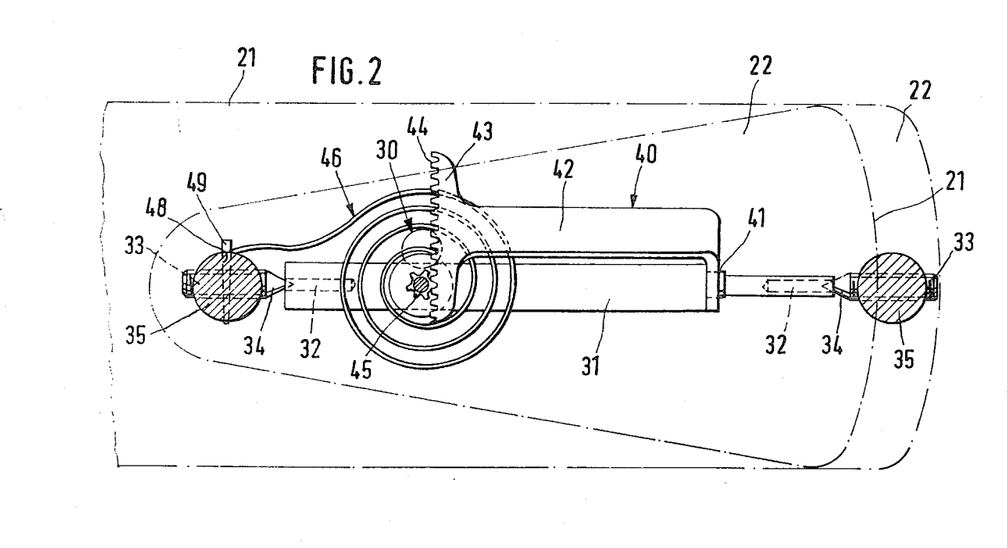
FIG. 2 shows, in a plan view, the drive mechanism of the pressure gauge of FIG. 1.

The magnification part of the drive mechanism 12 consists essentially of a drive arm 40 which is fixedly mounted on the sensing shaft 31. As can be seen in FIGS. 1 and 2, the drive arm 40 has an elongated flat body profile, one extremity having a bore by which the arm is seated on a matching diameter of the sensing shaft 31. The two parts are rigidly attached to each other by means of an upset on the sensing shaft opposite a supporting shoulder. From this attachment point, the drive arm extends first radially and then axially, its radial length portion 41 and its axial length portion 42 forming a right angle. The free extremity of the drive arm 40 is laterally enlarged in both directions, forming a yoke 43 (FIG. 2). The yoke 43 is bent along an arc, so as to have its inner and outer surfaces arranged concentrically with the rotational axis of the sensing shaft 31. The spatial location of the yoke 43 can thus be said to coincide with an axial extremity of a thin-walled tube. The side of the yoke 43 pointing away from its attachment to the axial length portion 42 is aligned with a radial plane through the sensing shaft 31. On this side, the yoke 43 carries a series of axially oriented gear teeth 44 which thus form a sector of a cup-type gear.

On the pointer shaft 20 is arranged a small pinion 45 whose teeth cooperate with the gear teeth 44 on the yoke 43 of drive arm 40. The two gears thus form an angle drive. The large difference in pitch radii of the drive arm gear teeth 44 and of the pinion 45 produces a corresponding magnification ratio from the angular displacements of the sensing shaft 31 to the angular displacements of the pointer shaft 20. The arrangement of the pointer shaft between axially adjustable threaded bearing pins 33, as described earlier, allows for a convenient position adjustment of the drive arm 40 in relation to the pinion 45, so that an optimal working clearance between the meshing teeth can be set at assembly.

As can best be seen in FIG. 1, the angular shape of the drive arm 40 lends itself readily to bending adjustments on that arm, especially with respect to its axial length portion 42. The particular configuration of the gear drive engagement between the gear teeth 44 of the drive arm yoke 43 and the pinion 45 thus makes it possible to change and adjust the drive ratio between these two gears, by simply changing the distance of the yoke 43 from its rotational center, i.e. from the sensing shaft 31. For this purpose, the axial length portion 42 of the drive arm 40 is bent upwardly or downwardly parallel to itself, using a suitable double bend of identical opposite angular deviation. This assures that the gear teeth 44 on the edge of the yoke 43 remain in alignment with a radial plane to the sensing shaft 31. However, such a shift in the pitch radius of the gear teeth 44 means that the previous concentricity of the gear teeth to the sensing shaft 31 is no longer present. Normally, this is of little consequence, but if necessary, it can readily be corrected by reshaping the arc of the yoke 45 accordingly.

Figure 4:
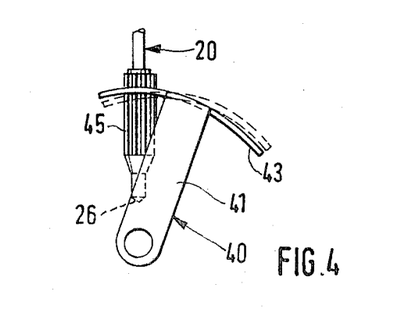
FIG. 4 shows a structural detail of FIG. 3, indicating adjustment features.

It may be desirable, on the other hand, to deliberately deviate from a constant magnification drive ratio between the sensing shaft 31 and the pointer shaft 20. This can be done in a most simple way by shaping the yoke 43 of the drive arm 40 in such a way that it deviates from concentricity with the axis of the sensing shaft 31. Such a possibility is indicated in FIG. 4, where a nonconcentric shape of the yoke is shown in dotted lines. The reason for intentionally incorporating such a non-linear drive ratio in the gear drive may be a desire to compensate for a non-linear characteristic of the pickup part of the drive mechanism 12 which converts lineal displacements of the diaphragm wall 15 into angular displacements of the sensing shaft 31. Of course, it is also possible to have a portion of the yoke 43 arranged concentrically with the sensing shaft axis, while one or both of its end portions are shaped to deviate from concentricity. In all cases, the clearance between the meshing teeth is sufficient to accommodate any resulting minor flank misalignments between the meshing teeth. It should be noted that the radial length of the gear teeth 44 of the drive arm is rather small.

In addition to the pointer 11 and the pinion 45, the pointer shaft 40 also carries a spiral spring 46 which serves as a return spring for the pointer by biasing the pointer shaft 20 in opposition to movements which indicate a rise in pressure. The spiral spring 46 is carried by a spring hub 47 which is seated on the pointer shaft 20 adjacent to the pinion 45. The inner extremity of the spiral spring 46 is attached to the spring hub 47, while the outer extremity of spring 46 is lodged and clamped in a tapered bore 48 in one of the spacer posts 23 by means of a suitable tapered pin 49 (see FIG. 2). The torque exerted on the pointer shaft 20 by the spiral spring 47 is in the direction of falling pressure, meaning that the pinion 45 on the pointer shaft will tend to move the drive arm 40 and its connected sensing shaft 31 and sensing member 30 in the direction towards the diaphragm wall 15 of the pressure capsule 10. Consequently, the sensing head 37 will at all times be preloaded against the wall portion 38 of wall 15, and the gears 44 and 45 will at all times be preloaded in one direction, thereby eliminating the effect of any flank clearance between the gear teeth. This arrangement provides assurance that the proposed gear drive gives a reliable, accurate pressure indication on the tip of the pointer 17, regardless of the exact radius and concentricity of the teeth-carrying yoke 43 with respect to the sensing shaft 31. In fact, this arrangement makes it possible for the drive arm 40 to be manufactured as a simple flat stamping which is later die-shaped and heat treated.

Figure 5:
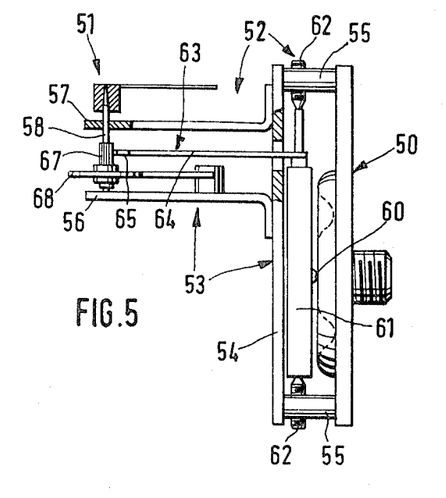
FIG. 5 shows, in elevation and partial cross section, a pressure gauge representing a second embodiment of the invention.
Figure 6:
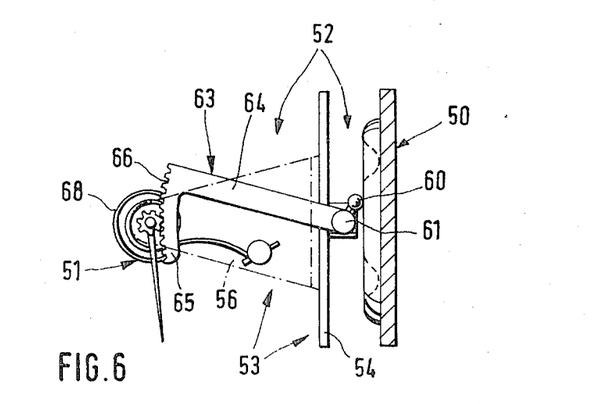
FIG. 6 shows the pressure gauge of FIG. 5 in a partially cross-sectioned plan view.

A second embodiment of the invention is illustrated in FIGS. 5 and 6. This pressure gauge consists of the same basic constituent units as the previously described embodiment, but, here, these units are arranged in a somewhat different structural relationship. The three constituent units of this pressure gauge are: a flexible capsule 50, a pointer 51, and a drive mechanism 52. A plate frame 53, of which only portions are shown in the drawing, supports and combines the three units. In the following, this second embodiment will be described only to the extent that it differs from the description given of the first embodiment of the invention. Reference should be had to the latter for features which remain unchanged, or substantially unchanged.

The plate frame 52 of FIG. 5 shows only a lower support plate 54, on the underside of which is mounted the pressure capsule 50, using spacer posts 55. The pressure capsule 50 itself is unchanged from the previously described embodiment. On the upper side of the support plate 54 are mounted two support brackets 56 and 57, the two brackets having upstanding parallel wall panels of generally triangular outline (stippled lines in FIG. 6). The support brackets 56 and 57 carry a pointer shaft 58, having for that purpose aligned journal bores similar to those previously described. The rotational axis of the pointer shaft 59 is thus aligned parallel to the support plate 54 and to the pressure capsule 50.

The drive mechanism 52 is similar to the one described further above, as far as its pickup features are concerned, a sensing member 60 on a sensing shaft 61 being biased against the diaphragm wall of the pressure capsule 50. The sensing shaft 61 is again journalled between two aligned threaded bearing pins 62 which engage center bores in the extremities of the sensing shaft 61. The sensing shaft 61 and the pointer shaft 58 are thus arranged in parallel alignment with one another.

The magnification part of the drive mechanism 52 is again provided by a pair of meshing gears, the latter being regular spur gears, however, due to the parallel alignment of their shafts. The large gear is again in the shape of a gear sector, formed by a drive arm 63 which has a straight radial arm portion 64 and a yoke portion 65. The attachment of the drive arm 63 to the sensing shaft 61 is the same as previously described. The drive arm 63 of this embodiment is a substantially flat stamping, its arm portion 64 and yoke portion 66 forming either an "L" shape, as shown in FIG. 6, or a "T" shape, similar to the yoke of the earlier embodiment. The outer periphery of the yoke 65 is concentric to the rotational axis of the sensing shaft 61, carrying regular spur gear teeth 66 which are oriented radially, for engagement with a pinion 67 on the pointer shaft 58. The pointer shaft 58 again carries a return spring in the form of a spiral spring 68 which exerts a unilateral rotational bias on the drive mechanism, for preloaded contact between the sensing member 60 and the pressure capsule 50, thereby eliminating any play in the drive mechanism 52. Unlike in the previously described embodiment, the gear drive ratio of the drive mechanism 52 is not adjustable.

The structural arrangement of the constituent units in accordance with FIGS. 5 and 6 produces a pressure gauge which is primarily suited for use in sphygmomanometers which require a right-angle arrangement between the pressure capsule and the indicating dial, or where the cost savings of a simplified drive mechanism override the advantages of a more complex drive mechanism which provides sophisticated adjustability of the displacement characteristics of the pointer.

It should be understood, of course, that the foregoing disclosure describes only preferred embodiments of the invention and that it is intended to cover all changes and modifications of these examples of the invention which fall within the scope of the appended claims.

I claim the following:

1. A pressure gauge of the type which gives a pressure indication by means of a rotating indicator comprising in combination:
    a pressure gauge frame;
    a sensing shaft journalled in the pressure gauge frame for rotation about a sensing shaft axis;
    pressure sensing means associated with the sensing shaft and operable to transduce and convert pressure values into corresponding angular displacements of the sensing shaft;
    a pointer shaft journalled in the pressure gauge frame for rotation about a pointer shaft axis which is oriented substantially perpendicularly to the sensing shaft axis, the pointer shaft carrying said rotating indicator; and
    a magnifying angle gear drive connecting the sensing shaft to the pointer shaft in such a way that small angular displacements of the sensing shaft create much larger angular displacements of the pointer shaft, the angle gear drive including a gear segment on the sensing shaft and a cooperating pinion on the pointer shaft; and wherein
    the pinion on the pointer shaft is a spur gear whose teeth are parallel to the pointer shaft axis;
    the gear segment is in the form of a drive arm, which has one extremity fixedly attached to the sensing shaft and includes on its other extremity a tooth-carrying yoke in the shape of a sector of a thin-walled tubular body, the teeth of the gear segment extending axially and in a radial plane with respect to the sensing shaft; and
    the gear segment defines a means for changing the mangification ratio of the angle gear drive to a higher or lower ratio by providing adjustability of the radial distance of the teeth-carrying yoke from the sensing shaft axis.

2. A pressure gauge as defined in claim 1, further comprising
    backlash-suppressing means for the angle gear drive in the form of a return spring on the pointer shaft.

3. A pressure gauge as defined in claim 2, wherein the pressure sensing means includes:
    a pressure capsule which is supported by the pressure gauge frame, defining an enclosed pressure chamber which is adapted for pressurization by a pressure medium, the pressure capsule having a wall portion in the form of a resiliently flexible diaphragm wall which executes expanding and contracting displacements, in response to increases and decreases of the pressure inside the pressure capsule and which is oriented substantially parallel to the sensing shaft, at a small distance therefrom; and
    a sensing member which extends substantially radially from the sensing shaft into contact with a sensing surface on the diaphragm wall of the pressure capsule which is located at a lateral distance from the sensing shaft axis; and wherein
    the return spring on the pointer shaft is rotationally preloaded in such a way that it creates a contact pressure between the sensing member of the sensing shaft and the diaphragm wall of the pressure capsule.

4. A pressure gauge as defined in claim 3, wherein the sensing member has a rounded head portion with which it is in contact with the sensing surface of the diaphragm wall and a threaded shaft portion engaging a threaded radial bore of the sensing shaft, thereby providing adjustability of the radial distance between the point of contact on the sensing surface and the sensing shaft axis.

5. A pressure gauge as defined in claim 1, wherein the gear segment further defines a means for skewing the magnification ratio of the angle gear drive into a nonuniform ratio by providing adjustability of the teeth-carrying yoke in such a way that at least a portion of its teeth is shifted out of concentricity with the sensing shaft axis, thereby making it possible to produce linear pointer shaft displacements from non-linear sensing shaft displacements.

6. A pressure gague as defined in one of claims 1–5, wherein
    the gear segment is in the form of an L-shaped drive arm, with a radial arm portion extending away from the sensing shaft and an axial arm portion carrying the yoke with the gear segment teeth; and
    said means for changing the gear drive magnification ratio is defined by a deformability of the axial arm portion of the gear segment, as a result of which the radial position of its teeth-carrying yoke is shiftable parallel to itself through a double bend in the axial arm portion.

7. A pressure gague as defined in claim 5, wherein said means for skewing the gear drive magnification ratio is defined by a deformability of the drive arm, as a result of which the teeth-carrying yoke is bendable out of its concentric relationship with the sensing shaft axis.

8. A pressure gauge of the type which gives a pressure indication by means of a rotating indicator comprising in combination:
    a pressure gauge frame;
    a sensing shaft journalled in the pressure gauge frame for rotation about a sensing shaft axis;
    pressure sensing means associated with the sensing shaft and operable to transduce and convert pressure values into corresponding angular displacements of the sensing shaft;

a pointer shaft journalled in the pressure gauge frame for rotation about a pointer shaft axis which is oriented substantially perpendicularly to the sensing shaft axis, the pointer shaft carrying said rotating indicator; and a magnifying angle gear drive connecting the sensing shaft to the pointer shaft in such a way that small angular displacements of the sensing shaft create much larger angular displacements of the pointer shaft, the angle gear drive including a gear segment on the sensing shaft and a cooperating pinion on the pointer shaft; and wherein the pinion on the pointer shaft is a spur gear whose teeth are parallel to the pointer shaft axis;

the gear segment is in the form of a drive arm, which has one extremity fixedly attached to the sensing shaft and includes on its other extremity a tooth-carrying yoke in the shape of a sector of a thin-walled tubular body, the teeth of the gear segment extending axially and in a radial plane with respect to the sensing shaft; and the gear segment defines a means for skewing the magnification ratio of the angle gear drive into a non-uniform ratio by providing adjustability of the teeth-carrying yoke in such a way that at least a portion of its teeth is shifted out of concentricity with the sensing shaft axis, thereby making it possible to produce linear pointer shaft displacements from nonlinear sensing shaft displacements.

9. A pressure gauge as defined in claim 8, further comprising backlash-suppressing means for the angle gear drive in the form of a return spring on the pointer shaft.

10. A pressure gauge as defined in claim 9, wherein the pressure sensing means includes:

a pressure capsule which is supported by the pressure gauge frame, defining an exclosed pressure chamber which is adapted for pressurization by a pressure medium, the pressure capsule having a wall portion in the form of a resiliently flexible diaphragm wall which executes expanding and contracting displacements, in response to increases and decreases of the pressure inside the pressure capsule and which is oriented substantially parallel to the sensing shaft, at a small distance therefrom; and a sensing member which extends substantially radially from the sensing shaft into contact with a sensing surface on the diaphragm wall of the pressure capsule which is located at a lateral distance from the sensing shaft axis; and wherein the return spring on the pointer shaft is rotationally preloaded in such a way that it creates a contact pressure between the sensing member of the sensing shaft and the diaphragm wall of the pressure capsule.

11. A pressure gauge as defined in claim 10, wherein the sensing member has a rounded head portion with which it is in contact with the sensing surface of the diaphragm wall and a threaded shaft portion engaging a threaded radial bore of the sensing shaft, thereby providing adjustability of the radial distance between the point of contact on the sensing surface and the sensing shaft axis.

12. A pressure gauge as defined in any one of claims 8–11, wherein said means for skewing the gear drive magnification ratio is defined by a deformability of the drive arm, as a result of which the teeth-carrying yoke is bendable out of its concentric relationship with the sensing shaft axis.

* * * * *